United States Patent
O'Farrell et al.

(10) Patent No.: US 12,071,616 B2
(45) Date of Patent: Aug. 27, 2024

(54) RNA TARGET ENRICHMENT OR DEPLETION OF BIOLOGICAL SAMPLES

(71) Applicants: Altratech Limited, Limerick (IE); The United States of America, as represented by the Secretary, Department of Health and Human Services, Rockville, MD (US)

(72) Inventors: Brian O'Farrell, Watergrasshill (IE); Claire O'Connell, Stamullen (IE); Kaylyn Oshaben, Summerhill, PA (US); Daniel Appella, Bethesda, MD (US)

(73) Assignees: Altratech Limited, Limerick (IE); The United States of America, as represented by the Secretary, Department of Health and Human Services, Rockville, MD (US)

( * ) Notice: Subject to any disclaimer, the term of this patent is extended or adjusted under 35 U.S.C. 154(b) by 352 days.

(21) Appl. No.: 17/193,652

(22) Filed: Mar. 5, 2021

(65) Prior Publication Data
US 2021/0277387 A1    Sep. 9, 2021

Related U.S. Application Data

(60) Provisional application No. 62/986,055, filed on Mar. 6, 2020.

(51) Int. Cl.
| | | |
|---|---|---|
| *C12N 15/10* | (2006.01) | |
| *C12Q 1/68* | (2018.01) | |
| *C12Q 1/6806* | (2018.01) | |

(52) U.S. Cl.
CPC ....... *C12N 15/1013* (2013.01); *C12Q 1/6806* (2013.01)

(58) Field of Classification Search
CPC . C12N 15/1013; C12Q 1/6806; C07K 14/003
See application file for complete search history.

(56) References Cited

U.S. PATENT DOCUMENTS

| 2007/0278111 A1 | 12/2007 | Boussaad et al. |
| 2015/0197793 A1 | 7/2015 | Armitage et al. |

FOREIGN PATENT DOCUMENTS

| WO | 2015/086652 A1 | 6/2015 |
| WO | 2015/086654 A1 | 6/2015 |
| WO | 2015/091139 A2 | 6/2015 |
| WO | 2016/091868 A1 | 6/2016 |

OTHER PUBLICATIONS

Hadziavdic, 2014, Characterization of the 18S rRNA Gene for Designing Universal Eukaryote Specific Primers, PLoS One 9(2):e87624.
Ratilainen, 1998, Hybridization of peptide nucleic acid, Biochem 37(35):12331-12342.
Weiler, 1997, Hybridisation based DNA screening on peptide nucleic acid (PNA) oligomer arrays, Nucleic Acids Research, 25(14):2792-2799.
Wu, 2017, Recent advances in peptide nucleic acid for cancer bionanotechnology, Acta Pharmacologica Sinica, 38:798-805.

*Primary Examiner* — Jezia Riley
(74) *Attorney, Agent, or Firm* — Brown Rudnick LLP; Adam M. Schoen

(57) ABSTRACT

A method of target enrichment or depletion from a sample with an analyte is described. A probe has one of a left-handed PNA pair and a targeting moiety, in which the left-handed PNA pair are a complementary pair of PNAs that are chiral and have a cyclic backbone modification that induces a left-handed helical structure. A capture surface has the other of the left-handed PNA pair; and the left-handed PNA pair bind to hybridize the probe to the capture surface, which may be a magnetic bead.

16 Claims, 14 Drawing Sheets

M = magnetic bead
= left-handed PNA
= linker
= antibody
= Target
$P_1$ = first probe for target containing left-handed PNA, linker and targeting antibody capture and tether of 18s rRNA from total human isolate at 37°C.
N=3 and the trend line is of the average values (grey dot).

capture and tether of 18s rRNA from total human isolate at 37oC. N=3 and the trend line is of the average values (grey dot).

RNA TARGET ENRICHMENT OR DEPLETION OF BIOLOGICAL SAMPLES

TECHNICAL FIELD

The invention relates to methods and devices for capturing target molecules of a biological sample.

BACKGROUND

Methods for RNA targeting and amplification often use enzymatic amplification methods, such as Polymerase Chain Reaction (PCR). Proper storage and handling of reagents is necessary in these methods. In addition, enzyme functionality is important to ensure success of the amplification process. One challenge is that enzymes are temperature-sensitive and have a limited shelf life.

Sequence-specific RNA enrichment or depletion may be achieved using biotin-avidin (or commonly streptavidin or neutravidin) affinity reactions in which a biotinylated probe that has a sequence complementary to a sequence of interest is captured on a streptavidin functionalized surface, such as, a microsphere.

Biotin-avidin is used extensively in applications such as enzyme linked immunosorbent assay (ELISA); immunohistochemistry (IHC); western, northern, and southern blotting; immunoprecipitation; cell surface labelling; affinity purification; fluorescence-activated cell sorting (FACS); and electrophoretic mobility shift assays (EMSA). A noted limitation is that all biotinylated molecules can bind to any biotin-binding molecule, thus reagents must be used in combination with other detection-probe systems (e.g. primary-secondary antibodies) for multiplex experiments. Importantly, naturally occurring biotin in samples has been found to cause false results in some tests and has been subject of warnings by the USFDA who have requested that lab test developers contact them to discuss. Food supplements containing biotin are a particular problem.

Furthermore, storage and transportation of streptavidin reagents present logistical challenges due to refrigeration needs. Sodium azide, a potentially explosive material, is commonly used to prevent bacterial growth during long term storage, and extensive washing steps are required to remove it from solutions to prepare beads and biologics before use.

SUMMARY

The present invention provides methods for capture of a target molecule in a biological sample. Methods of the invention utilize peptide nucleic acid (PNA) probes for capture and delivery of target molecules. In a preferred embodiment, a first chiral PNA probe comprising of a capture moiety is used to capture a target analyte and is then bound to a complementary second chiral PNA probe attached to a solid support. In a preferred embodiment, the PNA probes are left-handed chiral pairs. PNA probes of the invention may be attached to binding moieties via a linker. The binding moiety may be a nucleic acid, a glycol, a protein (including antibodies or enzymes), a small molecule, a carbohydrate or lectin, or any other binder that can attached to a target molecule. In one example, a PNA probe attached to a solid support captures, via hybridization, another PNA probe that is attached via a linker to another PNA probe that terminates in a binding moiety. The PNA probes preferably have left-handed chirality so that they hybridize with their PNA complementary binding pair but not with native RNA or DNA. The invention utilizes this approach to specifically capture a target molecule in a biological sample. The probe may comprise a linker linking the left-handed PNA with a targeting moiety. In an alternative embodiment, the capture probe may be a right-handed PNA molecule.

The solid support to which these "keychain" PNA molecules are attached may be any suitable solid support. For example, the solid support may be a surface of a bead or magnetic particle. As such, in certain embodiments a magnetic field may be used to manipulate (e.g., move or detect) analyte bound with a capture moiety. In some instances, the solid support is associated with a sensor or a sensor surface for sensing bound analyte. Advantageously, this arrangement permits samples of analyte to be rapidly detected by flowing or passing analyte bound to a capture moiety of a first chiral PNA molecule over the sensor surface having a second chiral PNA molecule complementary to the first chiral PNA molecule. Capture of the first chiral PNA molecule with the complementary chiral PNA molecule provides for analyte detection. Accordingly, methods of the invention are well suited for use with microfluidic systems. And since the chiral PNA molecules do not bind to other analyte (e.g., DNA or RNA), detection methods using the keychain PNA molecules offer reliable measurements of analyte in samples.

A hallmark of PNA is its stability and versatility. Methods of probing analyte using PNA molecules thus provides several distinct advantages over conventional DNA and RNA methods. For example, PNA molecules are resistant to degradation by nucleases and proteases and are stable even in acidic environments. This enhanced stability allows PNA molecules to capture targets even under sub-optimal conditions, such as, in acidic or low-salt solutions. Accordingly, methods of the invention, by relying on PNA molecules, can capture analyte from otherwise difficult to process samples, such as, cell lysates. Moreover, PNA molecules have a long shelf life (months to years) as compared to DNA or RNA, or the 6 months shelf life for streptavidin, and, because they are not prone to nuclease degradation, do not require refrigeration.

Methods of the invention do not require enzymes for detection or enrichment of nucleic acids. As such, the methods described herein are not constrained by the same strict operating conditions as similar methods involving enzymes. Moreover, in most instance, reagents used in the methods described herein do not require refrigeration. As such, methods of the invention can be used anywhere, such as in a remote location, and by anyone. For example, methods of the invention can be conducted across a broad range of temperatures, for example, a range of about 18° C. to about 80° C. Although, in preferred embodiments, methods of the invention are conducted at about 37° C.

PNA probes of the invention use capture moieties to bind analyte that is of interest. In some instances, the analyte may be a protein or a surface antigen of a cell. Capture moieties thus may include an antibody or antibody fragment. The antibody or antibody fragment of the capture moiety can be used to capture the antigen associated with analyte of interest. The PNA probe having the antibody capture moieties is preferably chiral. In use, a second chiral PNA probe, complementary to the antibody-linked PNA probe, may be used to capture the antibody-linked PNA probe bound with target analyte.

PNA probes of the invention may be part of a chain of PNA. The chain of PNA can include any number of nucleic acid monomers. Advantageously, since PNA is generally uncharged, PNA is associated with a higher binding strength than a similar oligonucleotide of DNA or RNA. Accordingly, PNA probes may capture a complementary target with fewer monomers than a similar oligonucleotide of DNA or RNA. In some embodiments, the PNA probes of the invention comprise fifteen or fewer nucleic acid monomers. Moreover, in certain embodiments described herein, methods of the invention contemplate modifying a charge of PNA. Preferably the PNA is chiral. Modifying the charge of a PNA molecule, e.g., making the PNA molecule negatively charged, is useful to reduce binding affinity of the PNA to other negatively charged nucleic acids (e.g., DNA or RNA), thereby increasing binding specificity for complementary chiral PNA.

Methods of the invention are particularly useful for multiplexing. Since left-handed chiral PNA probes of the invention bind specifically with complementary sequences of other left-handed chiral PNA probes (and not other nucleic acids), the probes are easily programmable for multiplex reactions. For example, the left-handed PNA probes can be altered by length and/or monomer sequence to differentially bind other complementary probes. As such, according to some methods, a plurality of different left-handed chiral PNA probes, bound with different target analyte, can be differentially captured and/or detected by corresponding left-handed PNA probes comprising complementary sequences.

In some embodiments, PNA probes of the invention include a linker. Preferably, the linker links the PNA probe to a capture moiety. The linker may comprise a cleavable bond. For example, the linker may comprise a bond that is cleavable by a protease to thereby allow captured analyte to be separated from PNA probes for downstream processing. The linker can be of a length of 1 to 120 atoms, and/or may include any one or more of the elements: C, N, O, S, P, and Si. The linker may be in a chain that contains one or a combination of the following: a single bond, a double bond, a triple bond, an amide bond, an ester bond, a disulfide bond, an imino group, an ether bond, a thioether bond, and a thioester bond.

In another aspect, the invention relates to a target enrichment or depletion apparatus for performing methods of the invention. The apparatus includes a chamber for binding analyte with probe comprising a left-handed PNA molecule linked to a capture moiety. The chamber may provide a surface comprising complementary left-handed PNA probed bound with analyte. The surface may be one or more beads. The one or more beads may be releasable from a compartment of the apparatus. For example, the beads, having PNA probes, may be packaged in a heat-sensitive substrate, e.g., a wax, inside a compartment of the chamber. The beads may be released into the chamber after the probe has bound with analyte by applying heat. Preferably the PNAs comprises pairs of a complementary PNAs that are chiral and have a cyclic backbone modification that induces a left-handed helical structure.

DETAILED DESCRIPTION

Figure 1:
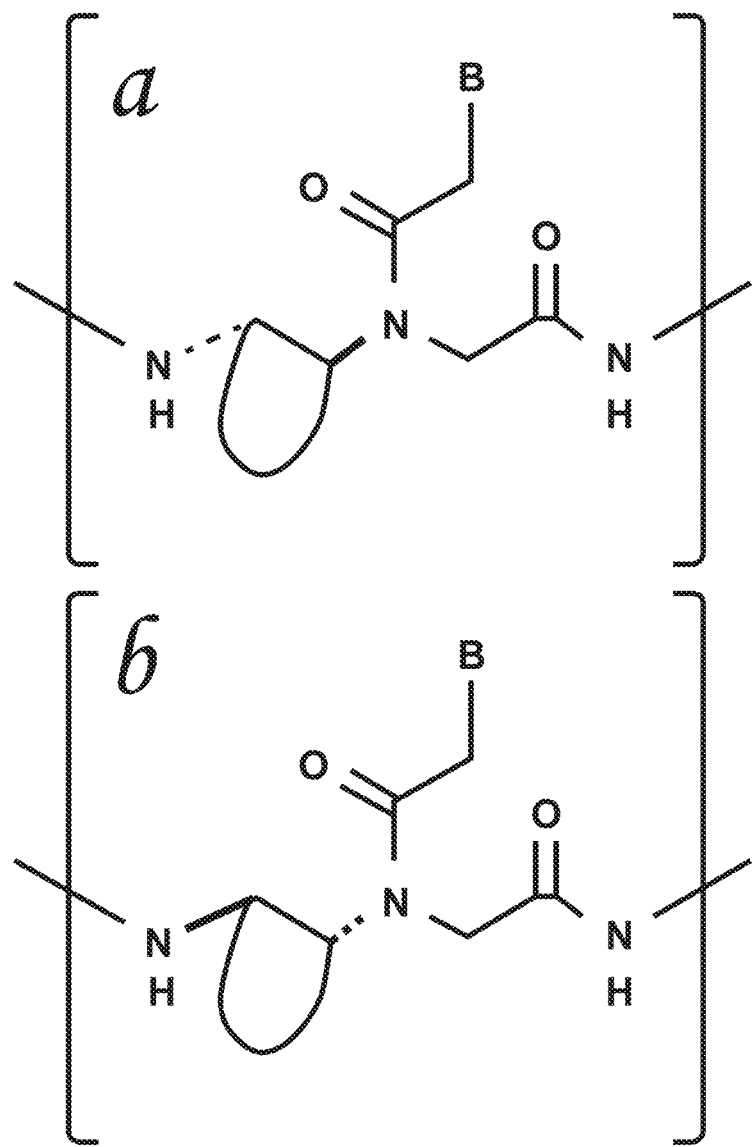
FIG. 1 shows two modified monomers useful to induce chirality.

The invention relates to assays for capturing target molecules from biological samples. More particularly, the invention relates to assays that use modified peptide nucleic acids (PNAs) for capturing target analyte. Preferably, the PNAs are modified by the incorporation of certain monomers (described below) to induce chirality. The invention takes advantage of the induced chirality to manipulate binding affinities of the PNAs for non-PNA molecules. In particular, preferred methods of the invention induce chirality in PNAs to reduce the binding affinity of PNAs for DNA and/or RNA in a sample, which thereby increases selectivity of PNAs for other modified PNA molecules.

PNAs are oligonucleotide analogues in which the sugar-phosphate backbone has been replaced by a pseudopeptide skeleton. The backbones of PNAs generally include uncharged repeats of N-(2-aminoethyl) glycine units (AEG) linked by peptide bonds. The synthetic backbone provides PNAs with many beneficial properties, such as, a low dependency on ionic strength, high chemical stability, high sequence specificity and resistance to both nucleases and proteases. In some instances, they bind to DNA and/or RNA with high specificity and selectivity, leading to PNA-RNA and/or PNA-DNA hybrids that are more stable than the corresponding nucleic acid complexes. For further discussion on hybridization of nucleic acids using PNA, see Ratilainen, 1998, Hybridization of Peptide Nucleic Acid, Biochemistry 1998, 37, 35, 12331-12342, and Weiler, 1997, Hybridisation based DNA screening on peptide nucleic acid (PNA) oligomer arrays, Nucleic Acids Research, Volume 25, Issue 14, 1 Jul. 1997, Pages 2792-2799, each of which are incorporated by reference.

It is an insight of the invention that the binding affinity and selectivity of the PNAs for nucleic acids (e.g., RNA) can be modified by the introduction of stereogenic centers (e.g., D-Lys-based units) into the PNA backbone, thus making modified PNAs ideal candidates for target capture methods. In preferred embodiments, methods of the invention use modified PNAs synthesized to have left-handed chirality.

Naturally occurring nucleotides like DNA and RNA, have a right-handed chirality, of which, achiral and right-handed PNA can bind to and can be used to target these nucleotides. However, the naturally right-handed oligonucleotides do not generally bind to left-handed chiral PNA, due to the incompatibility of the helical structures, which prevents traditional Watson-Crick base pairing from occurring. Thus, left-handed PNAs are generally only capable of binding to other left-handed PNAs or achiral PNAs. Thus, chiral PNAs are associated with less stable PNA-DNA duplexes than their achiral analogues. This effect can be more pronounced in methods of the invention using modified PNA backbones containing amino acids with bulky non-polar side chains, or negatively charged monomers (based on either D- or L-aspartic and glutamic acids) that create repulsive interactions with the negatively charged phosphate groups of the DNA.

These properties make left-handed PNAs ideal candidates for use in a capture system, where the components of the capture system do not interact with naturally occurring nucleotides. In particular, left-handed PNAs, according to methods of the invention, are employed as components of a probe. The probe also includes a targeting moiety and, preferably, a linker linking the left-handed PNA to the targeting moiety. In certain embodiments, left-handed PNAs are also used as components of beads or are fixed to a sensor surface for detection of the target.

FIG. 1 shows two modified monomers useful to induce chirality. In particular, shown are two enantiomers of cyclic PNA backbone modified monomers 103, 105 that induce (a) left-handed 103 and (b) right-handed 105 chirality. The helical structure of a PNA can be influenced by the inclusion of these monomers within the PNA sequence.

The PNAs can be synthesized by methods known in the art, for example, as described in Wu, 2017, Recent advances in peptide nucleic acid for cancer bionanotechnology, Acta Pharmacologica Sinica volume 38, pages 798-805, which is incorporated by reference. Preferably, the PNAs are made with one or more of the modified monomers. A PNA sequence without one of the modified monomers may not have a preferred helical structure and as such, may be achiral. If at least one cyclic backbone modified monomers 103, 105 is included, the constrained backbone structure induces either left-handed (a) or right-handed (b) chirality in the PNA. The inclusion of more than one monomer may be desired to ensure the chirality preference of the entire length of PNA. The chirality of the PNA may be assessed by various techniques known in the art. For example, a PNA synthesized to include one or more of the monomers can characterized by nuclear magnetic resonance or by x-ray crystallography.

Methods of the invention incorporate stereocenters into PNAs to make pairs of left-handed PNAs. The left-handed pairs refer to a complementary pair of PNAs that are chiral and have at least one cyclic backbone modification monomer that induces a left-handed helical structure. They are sometimes in this specification referred to as "left-handed PNA pairs". They are not to be confused with gamma PNAs, which have a different backbone chemistry but can be left-handed.

The left-handed PNAs are enantiomers to right-handed cyclic modified backbone PNAs which can be used as a targeting moiety for nucleic acids. However, as described below, the targeting or capture moiety is not limited to PNAs.

The left-handed PNA pairs are used in various manners to provide assays with target enrichment of biological entities such as RNA, in which the target molecules in a sample are for example attached to beads (for example magnetic beads) or to a surface for analysis by a sensor such as a capacitive sensor. The left-handed PNA can also be used to remove a relatively abundant target in a depletion type assay leaving rarer targets behind for further detection or analysis.

For example, in preferred embodiments, a first chiral PNA molecule linked with a capture moiety is used to capture a target molecule (e.g., RNA). The first chiral PNA molecule bound with the target molecule, via the capture moiety, is then captured with a complementary chiral PNA molecule that is preferably attached to a solid support. In a preferred embodiment, the PNA molecules are left-handed chiral pairs. The PNA molecules of the invention may be attached to capture moieties via a linker. The capture moiety can be any moiety that binds with the target molecule, for example, the capture moiety may be a nucleic acid, a glycol, a protein (e.g., an antibody or antibody fragment), a small molecule, a carbohydrate or lectin, or any other molecular binder that can attach to the target molecule.

In one example, a PNA probe attached to a solid support captures, via hybridization, another PNA probe that is attached via a linker to another PNA probe that terminates in a binding moiety. The PNA probes preferably have left-handed chirality and thus hybridize with specifically to complementary chiral PNA binding partner but not with native RNA or DNA. The invention utilizes this approach to specifically capture a target molecule in a biological sample.

Advantageously, in some examples a PNA probe is first hybridized to its target sequence (in one example 18s ribosomal RNA) and subsequently to the bead, using a left-handed PNA pair. This is referred to in this specification as a "two-step" approach. This approach achieves much improved target enrichment compared to an approach of the probe being initially bound to the bead.

In some instances, probe is attached to a sensor surface. For example, the probe may be attached to a surface of a sensor as described in WO 2015/086654; WO 2015/091139, which are incorporated by reference. Attachment generally involves a left-handed PNA comprising a capture moiety hybridizing to a left-handed PNA complement attached to a surface. An achiral PNA could replace one or both of the left-handed PNA probes in this application. Achiral PNAs exhibit similar hybridization behavior towards complementary achiral, right- or left-handed PNAs; however, removal of the left-hand inducing backbone modification in one or both of the complementary pair of PNAs eliminates the abiotic nature of the probe capture and may introduce potential cross-hybridization with endogenous oligonucleotides.

Figure 2:
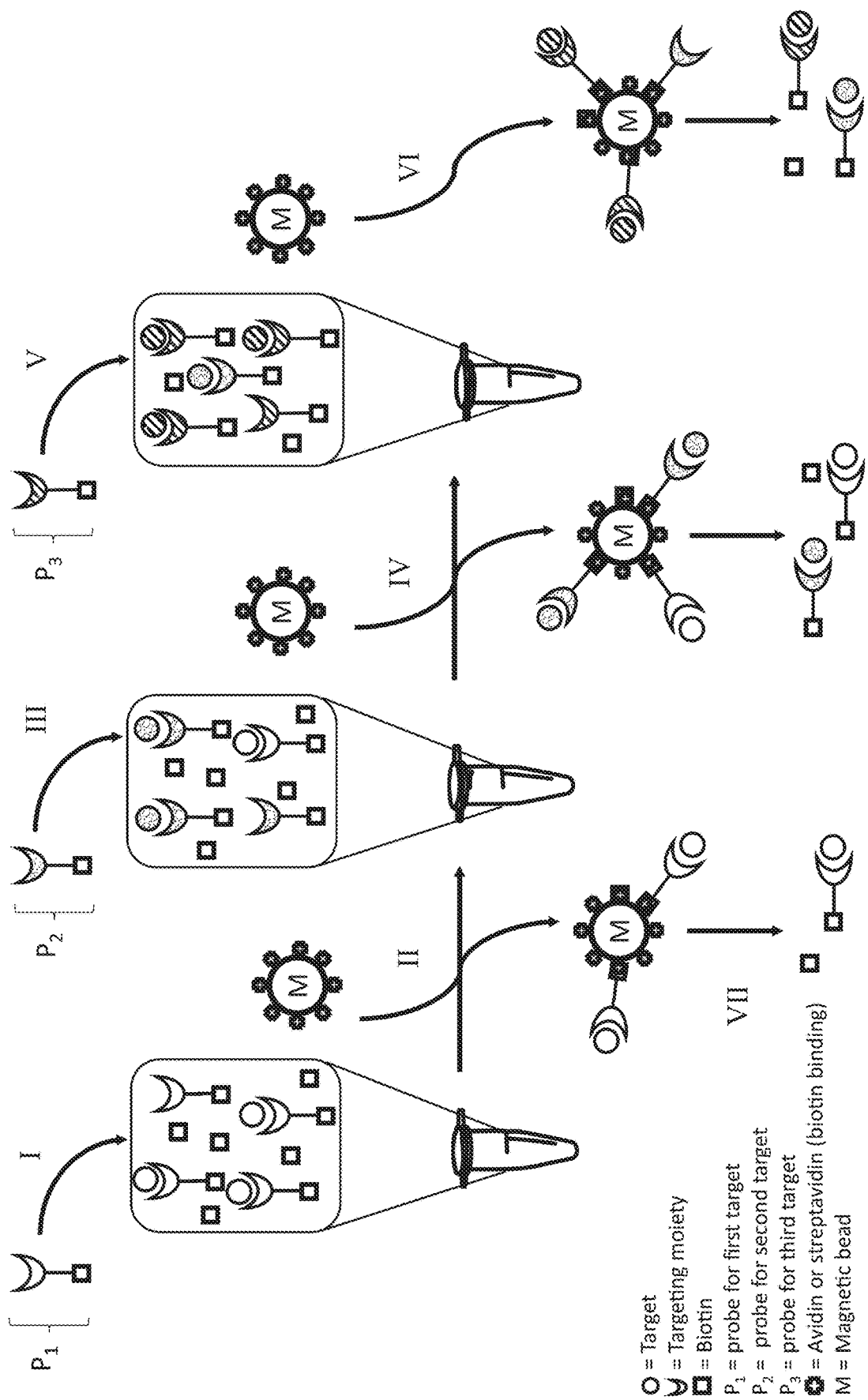
FIG. 2 shows a process for a multiplexing assay with biotin-streptavidin magnetic beads.

FIG. 2 shows a process for a multiplexing assay with biotin-streptavidin magnetic beads. The process, by way of comparison with the invention, provides for a multiplexing assay using a biotin-streptavidin magnetic bead system. The biotinylated probe for target one (P1) is incubated in the sample (I) followed by addition of a streptavidin coated magnetic bead (II). The beads with captured probe and target are removed. The same process of probe incubation and target removal by streptavidin-coated magnetic beads is followed for subsequent targets (III-VI). The target-probe complex is then removed from the beads (VII). Unlike the left-handed PNA system, there can be potential interference from endogenous biotin molecules and cross contamination from probes/targets not completely removed from previous steps due to the capturing moiety being biotin-streptavidin in all steps. The left-handed PNA system is not affected by endogenous or dietary biotin, as shown in FIG. 3.

Figure 3:
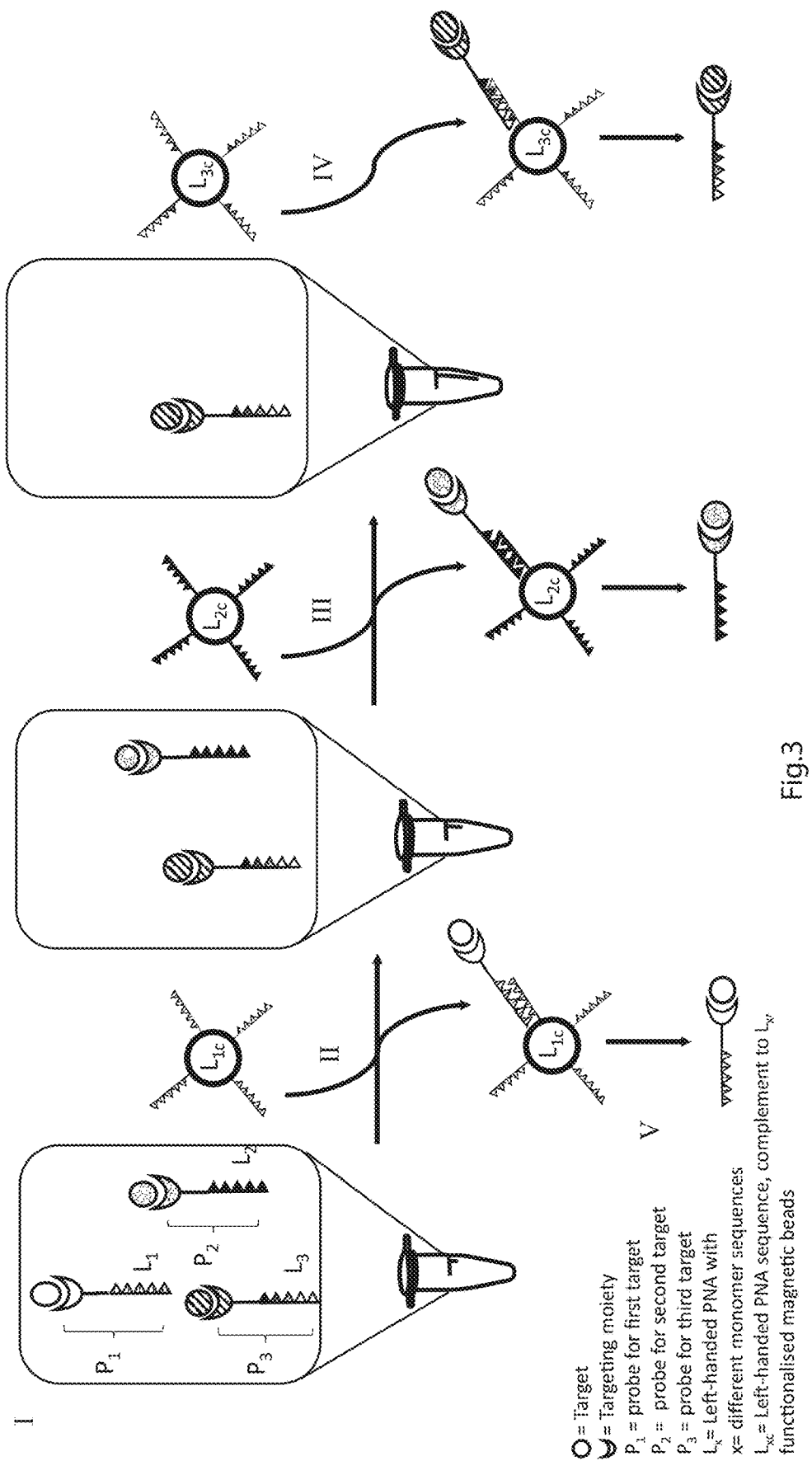
FIG. 3 shows a multiplexed assay with left-handed PNAs.

FIG. 3 shows a multiplexed assay with left-handed PNAs. The figure demonstrates the ability to perform a multiplexed assay of the invention by utilizing the programmability of the left-handed PNA system. In this example, there are three probe-bead sets, each having a different target (P1-3) and different left-handed PNA pairs (L1-3, L1c-3c). All three probes may be incubated in the sample at the same time (I). Magnetic beads coated with complementary left-handed PNAs are then sequentially used to remove the complementary probe and target (II-IV) without cross contamination from the other probes or native biomolecules. The bead-probe-target complex may be washed and the probe-target can be separated (V) from the beads, via heating, for further analysis. Because each target is captured using a unique probe pair, there is minimal cross contamination between probes and no interference from native DNA/RNA because of the left-handed chirality of the PNA.

The probes with left-handed PNAs can either have the same left-handed PNA on all probes or have different left-handed sequences on each probe so that different sets of beads functionalized with their complement can be used to capture a specific target. Accordingly, methods of the invention can be highly customized for various multiplexing applications. The PNA monomer sequence can be modified to any arrangement of sequence and they do not have any interaction with naturally occurring nucleic acids when removed at heat for stringency, as shown, for example, in FIG. 15.

Figure 4:
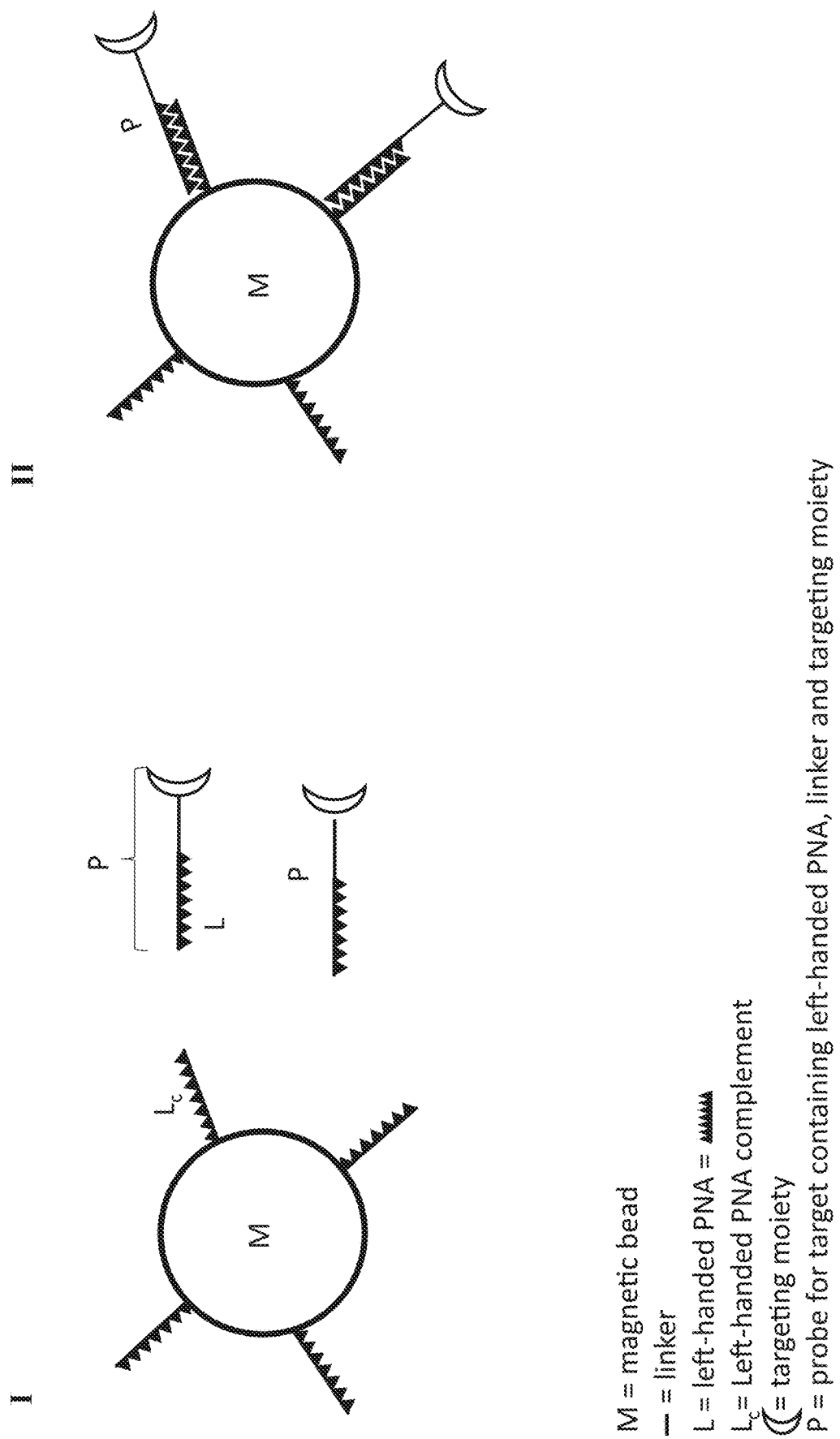
FIG. 4 is a schematic showing hybridization of a probe (P) to a magnetic bead.

FIG. 4 is a schematic showing hybridization of a probe (P) to a magnetic bead. In particular, shown are two illustrations, i.e., I and II, illustration I shows the components of the system and illustration II shows the interaction of those components.

The left-handed PNA (L) on the probe (P) hybridizes to magnetic beads (M) functionalized with a left-handed PNA complement (Lc), in which the complementary pair of PNAs are chiral and have a cyclic backbone modification that induces a left-handed helical structure. In some embodiments, pairs of left-handed PNAs are used for hybridizing. Illustrated is a probe (P1) hybridizing to a magnetic bead (M), which is common to many of the embodiments of the invention. The hybridization is effective, and allows, for example, use of beads in a sample and use of separate probes which already be bound to targets and/or detection moieties, or, alternatively, may be bound after hybridizing to the beads.

In other examples, a fixed substrate, i.e., surface, is functionalized with a left-handed PNA (Lc) and probes such as the probe P hybridize to the surface for subsequent capture of targets or are already bound to targets and the capture on the fixed surface allows sensing. The sensing may for example be capacitive on the sensor, or it may be by way of radiative or non-radiative detection.

Figure 5:
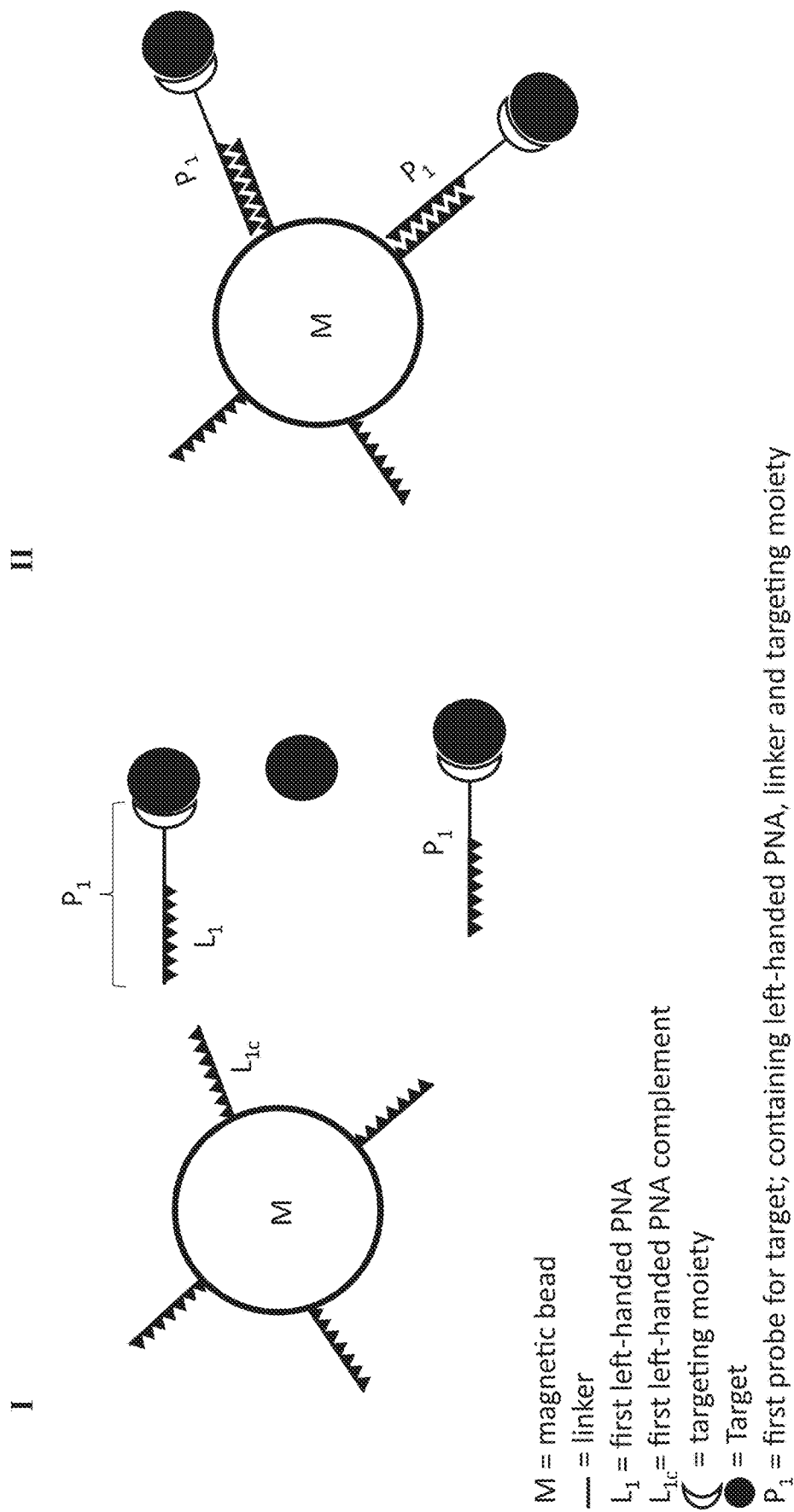
FIG. 5 shows target capture by hybridization.

FIG. 5 shows target capture by hybridization. Specifically, FIG. 5 shows (I) hybridization of a first probe P1 to a target by way of a targeting moiety (sometimes referred to herein as a capture moiety), and (II) hybridization of the probe to a magnetic bead M by way of a left-handed PNA pair. In this case the probe P1 has already attached to the target and by then binding to the bead allows the target to be conveyed in a microfluidic flow for example.

Figure 6:
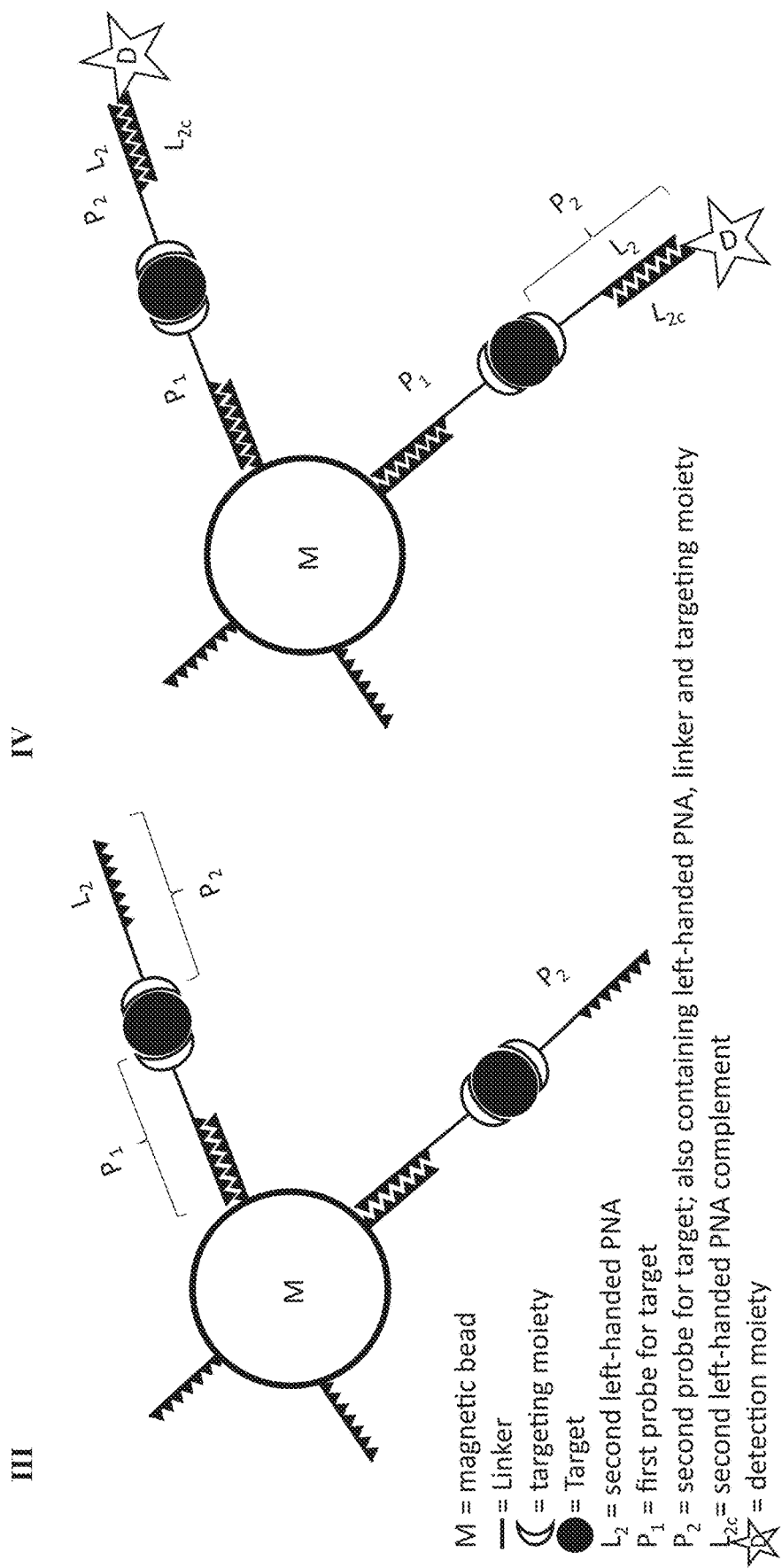
FIG. 6 shows an assay additional steps of target capture.

FIG. 6 illustrates additional steps of target capture. In particular, FIG. 6, which progresses from FIG. 5, shows (III) a second probe (P2) binding to the target, and (IV) hybridization of the second probes to detection moieties by left-handed PNA pairs. This allows sensing by way of fluorescent sensor of a type well known in the art. The detection moiety may be of any known type suited to the application.

This example shows how a chain of multiple entities involved in an assay may be chained together using left-handed PNA pairs, in this case bead-to-probe, and probe-to-detection moiety, with an in-between link of both probes to a target.

Figure 7:
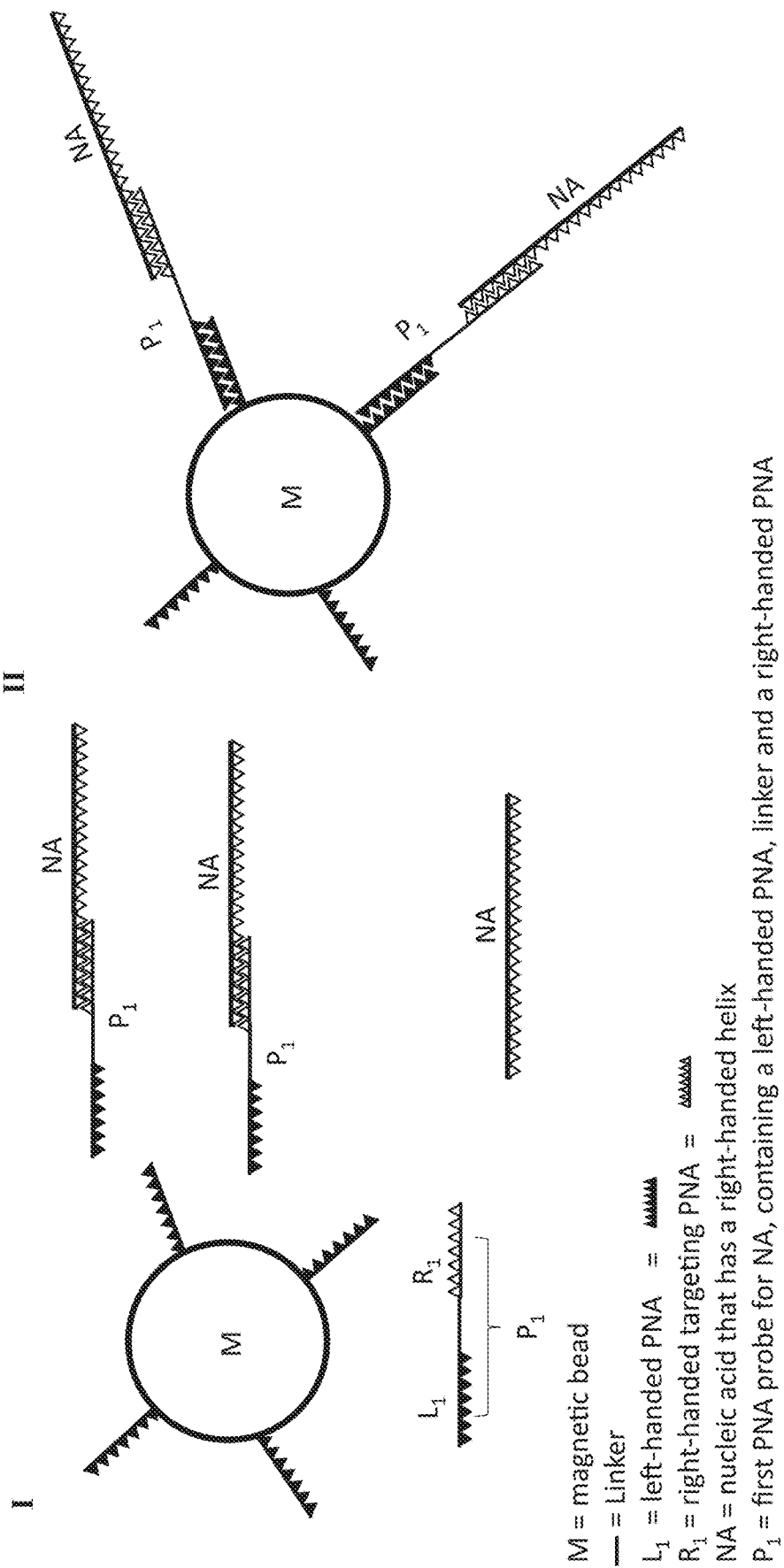
FIG. 7 illustrates use of a right-handed targeting PNA.

FIG. 7 illustrates use of a right-handed targeting PNA. In particular, FIG. 7 shows use of probe (P1) having a right-handed targeting PNA, a linker and left-handed PNA, in which (I) the probe hybridizes to a target nucleic acid sequence by way of its right-handed targeting PNA, and (II) the probe hybridizes to the beads by way of a left-handed PNA pair. This illustrates that a probe may have one of a left-handed PNA pair, a linker, and any suitable attachment entity such as in this case a right-handed targeting PNA R1.

Figure 8:
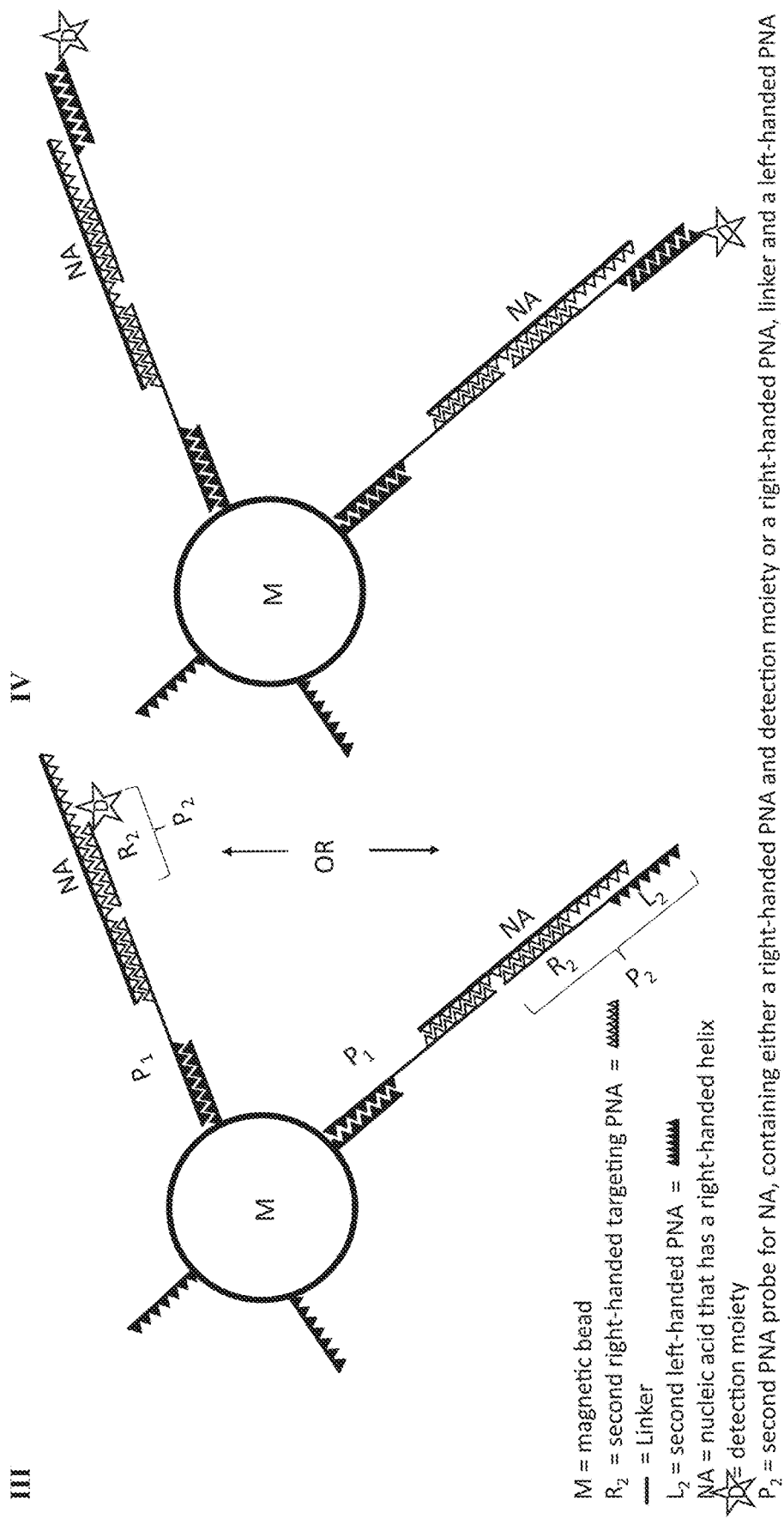
FIG. 8 shows additional steps of the method shown in FIG. 7.

FIG. 8 shows additional steps of the method shown in FIG. 7. In particular, FIG. 8 is an extension of the FIG. 7 mechanism, in which (III) a probe (P2) has a second right-handed targeting PNA (R2) attaching to a target NA, and (IV) a detection moiety is attached by a second left-handed PNA pair.

Figure 9:
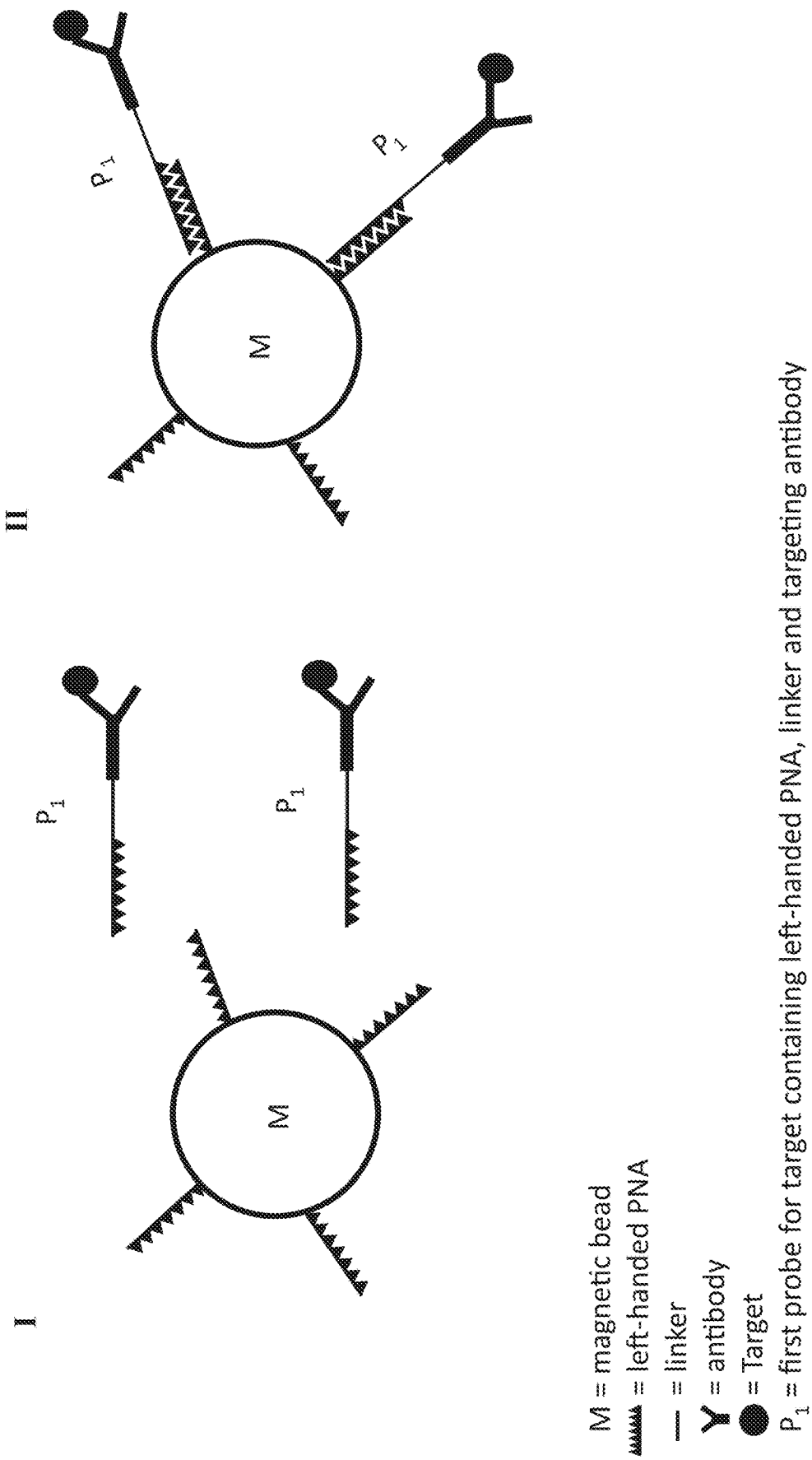
FIG. 9 shows an assay involving a targeting antibody.

FIG. 9 shows an assay involving a targeting antibody. In particular, FIG. 9 shows an assay in which (I) a probe P1 has a targeting antibody, a linker, and a left-handed PNA, and (II) it hybridizes to beads (M) by way of the left-handed PNA.

Figure 10:
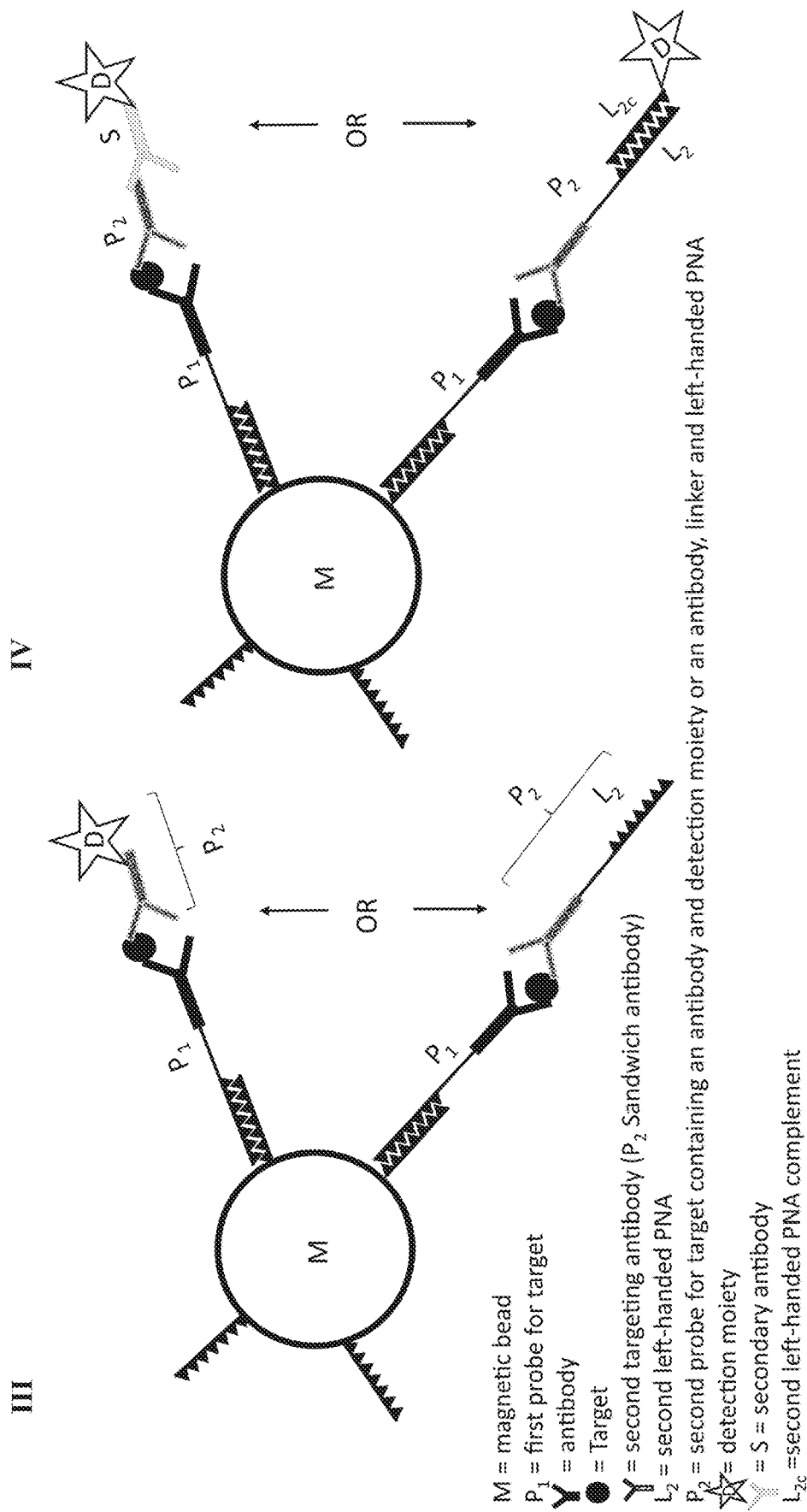
FIG. 10 is a continuation of the assay of FIG. 9.

FIG. 10 is a continuation of the assay of FIG. 9. In particular, FIG. 10 shows a development of an assay from FIG. 9, in which (III) the probe (P1) antibody attaches to a second probe (P2) with a detection moiety or has a second left-handed PNA (L2), and (IV) the second probe binds to a second antibody with a detection moiety or second left-handed PNA complement.

PNA conjugated beads and enrichment of RNA and tethering with fluorescent achiral PNA is achieved in various examples. The use of left-handed PNA pairs has been demonstrated to efficiently capture long and structurally complex RNA. There are many assays which benefit from a mechanism in which in the first step, a PNA probe that was free in solution, hybridizes the target RNA. In a second step, magnetic beads in the form of, for example, microspheres (such as "Dynabeads"), which have been functionalized with a left-handed PNA complementary to the left-handed PNA probe bound to the target RNA, are introduced.

18s ribosomal RNA is a long and structurally complex RNA that is used as an endogenous control for many RT-qPCR reactions because of its abundance and consistent expression between cells, even in those that have been infected with influenza, that make 18s ideal for normalization with target sequences. For the same reasons as it's use in PCR, it is therefore of interest in this assay. It has been shown that using the two-step hybridization, 18s ribosomal RNA can be captured from a total human RNA isolate much more efficiently than with a capture achiral or right-handed PNA that is covalently attached to the microspheres. Furthermore, 18s ribosomal RNA can be enriched from different biological backgrounds, either of blood or saliva using this method.

In one aspect, the invention provides a method of target enrichment. The method includes the steps introducing a probe comprising a left-handed PNA molecule linked to a capture moiety into a sample comprising target analyte. The sample may be any biological sample. For example, the sample may be a fluid sample, such as, blood, saliva, or urine, taken from a subject. Target analyte preferably comprises RNA. The RNA may be RNA of a pathogen. For example, in preferred embodiments, the target RNA is 18S ribosomal RNA (abbreviated 18S rRNA). Preferably, the 18S rRNA comprises variable nucleic acid sequences for use in identifying and/or characterizing a biological species, for example, as described in Hadziavdic, 2014, characterization of the 18S rRNA Gene for Designing Universal Eukaryote Specific Primers, PLOS One 9(2): e87624, incorporated by reference.

Probes of the invention comprise left-handed PNA molecules comprising capture moieties, which are preferably achiral or comprise right-handed chirality. The left-handed PNA molecules may comprise a single-stranded sequence of PNA comprising a sequence complementary to a partner left-handed PNA probe. The sequence may comprise an number of nucleotide bases, for example, 2, 5, 10, 15, 20, 25, or more bases.

The method involves capturing, with the capture moiety, the target analyte. Capturing may involve binding by complementary base-paring of the capture moiety to the target analyte. The capture moiety may comprise an oligonucleotide having a sequence complementary to the analyte. The oligonucleotide may comprise DNA or RNA. The capture moiety may comprise a right-handed PNA. The capture moiety may be linked to the left-handed PNA molecule by a linker. The linker may comprise one or more nucleic acids. Capturing may involve contacting sample having target analyte with PNA probes under conditions that allow the capture moiety probe sequence to hybridize with its complementary sequence of target analyte. The probe may be labeled with a radioactive or chemical tag that allows its binding to be visualized.

The method further involves binding the left-handed PNA molecule with a complementary PNA molecule comprising a left-handed chiral structure. The complementary PNA molecule is preferably attached to a surface to thereby enrich for target analyte. The surface may be a surface of a bead. The bead may be a magnetic bead, such as the magnetic bead sold under the trade name Dynabead by ThermoFisher. Alternatively, the surface may comprise a surface associated with a sensor for detecting analyte.

In one aspect, the invention relates to a target enrichment or depletion apparatus for performing methods of the invention. The apparatus includes a chamber for binding analyte with probe comprising a left-handed PNA molecule linked to a capture moiety. The chamber may provide a surface comprising complementary left-handed PNA probed bound with analyte. The surface may be one or more beads, such as, magnetic beads. The one or more magnetic beads may be releasable from a compartment of the apparatus. The compartment may be a compartment in a lid of the apparatus. For example, the beads, having PNA probes, may be packaged in a heat-sensitive substrate, e.g., a wax, inside a compartment of the chamber. The beads may be released into the chamber by heating the apparatus after the probe has bound with analyte by applying heat. Releasing the beads comprising complementary probe effectively tethers analyte to the magnetic beads. A magnet associated with the apparatus can be used to draw the analyte bound beads into molten wax, which can be resolidified by cooling. Preferably the PNAs comprises of pairs of complementary PNAs that are chiral and have a cyclic backbone modification that induces a left-handed helical structure. For example, the apparatus may be a sample apparatus as described in WO/2015/086652 or 2016/091868, each of which are incorporated by reference.

Examples 18s ribosomal RNA (rRNA) was used as the target sequence and PNA probes were designed. One of the designed probes, which was called 458R and will be referred to as the 458R sequence herein, was synthesized in three versions.

The first PNA, '458R' was an achiral PNA. The second was '458R RH', a right-handed chiral version of the same sequence as 458R. The third was a PNA probe, which had a 458R RH PNA on one end and was linked to a left-handed chiral PNA called 'LH PNA-458R RH'. Superparamagnetic Dynabeads (1 μm) were functionalized with either the 458R or 458R RH PNA directly onto the bead, and for the case of the 'LH PNA-458R RH' the complement of the left-handed PNA sequence was functionalized on the bead.

Results

Previous data with a fluorescently labelled synthetic short RNA sequence (28 bases) gave approximately 80% capture of the RNA at 57° C. in PBS containing 0.05% Tween 20, for all sets of beads that were functionalized with 5 μM of PNA. These beads were then tested with a real 18s ribosomal RNA from a total human RNA isolate. 1 μg (or 0 μg in control wells) of total human RNA was hybridized either; directly to the 458R or 458R RH functionalized Dynabeads™ for 10 mins, or alternatively, first hybridized to the 'LH PNA-458R RH' PNA probe for 10 mins before another 10 min incubation to the left-handed complement beads, all at 57° C. in PBS buffer containing 0.05% Tween 20. In order to measure the amount of RNA that was specifically captured by the beads, an Atto488 fluorescently labelled achiral PNA was hybridized with the captured 18s rRNA, for 10 mins at 57° C.

The fluorescent PNA was hybridized after the beads had been washed to remove non-specifically bound RNA and the specific 18s RNA had been subsequently brought into a well using the magnetic Dynabeads. Following the tethering of the fluorescently labelled PNA to the 18s rRNA, the beads were washed again to remove non-specifically bound PNA. Finally, the hybridized PNA was eluted off the RNA on the Dynabeads using a 10 mM potassium hydroxide solution and a heat step of 95° C. for 2 mins. The eluted PNA was measured fluorescently on a plate reader and the results of the experiment are shown in FIG. 11, which shows capture and tether of 18s rRNA from total human RNA using the different PNA capture systems.

Figure 11:
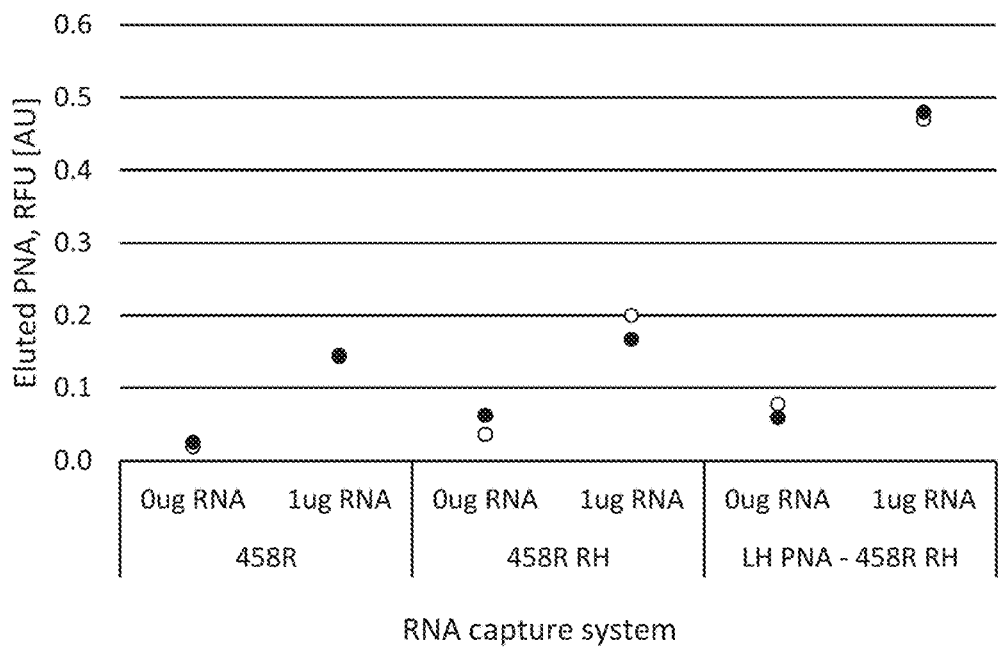
FIG. 11 shows data from capture and tether of 18s rRNA from total human RNA.

Data from FIG. 11 shows that some 18s rRNA was captured from a total human RNA isolate by each set of beads as the fluorescence was larger than the no-RNA control wells, in all cases. For the 458R PNA the difference between the RNA and no-RNA control wells was 0.12 and for the 458R RH PNA beads, it was similarly, 0.13 fluorescence units. However, the largest difference was seen for the two-step system with 0.41 fluorescence units difference. The 458R only captured 40% of the amount of RNA that the 'LH PNA-458R RH' set captured.

Figure 12:
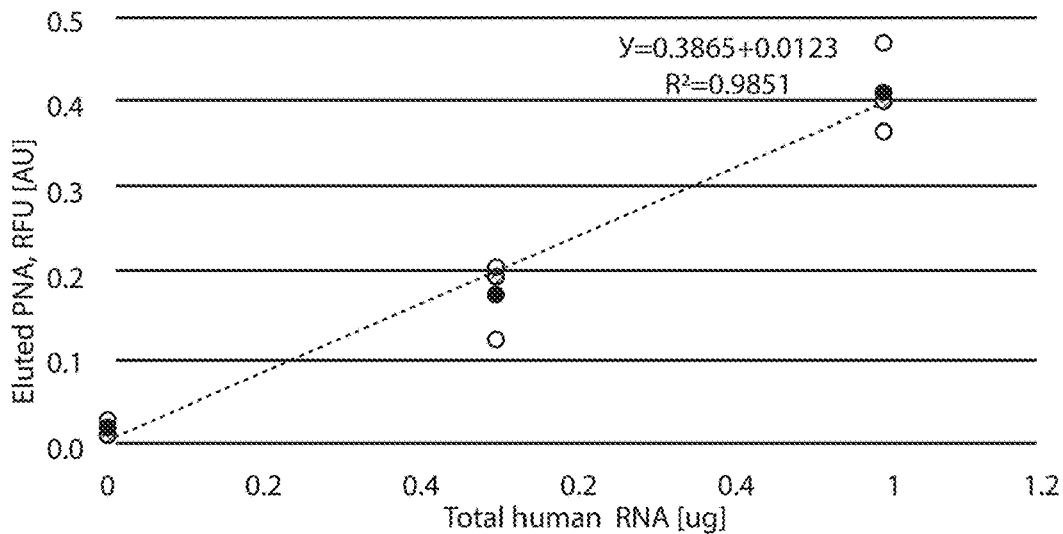
FIG. 12 shows data from the capture and tether of 18s rRNA from total human isolate.

Tethering using a fluorescent achiral PNA was used in all experiments to simulate a second PNA probe that may alternatively be used with the capture system. One advantage of using the left-handed PNA system is that RNA enrichment or depletion can be done isothermally at biologically compatible temperatures. Referring to FIG. 12, an experiment to demonstrate this was carried out, where hybridization of the probe and the Dynabeads was performed at 37° C.

FIG. 12 shows capture and tether of 18s rRNA from total human isolate at 37° C., N=3 and the trend line is of the average values (grey dot).

A linear trend was observed for tethering 18s rRNA at 37° C., ordinary body temperature, which implies that the capture and tethering do not rely on high temperatures for hybridization to the RNA. The amount of PNA eluted for the 1 μg and 0 μg of RNA are similar to those previously found as shown in FIG. 11 which was performed at 57° C., which implies that high temperatures are not needed for accessing the target sequence using the 'LH PNA-458R RH' probe, or improving specificity. This consequently means that minimal hardware and instrumentation is required to perform the assays and a simple heating step, which will simplify the final instrument, as thermal cycling is not required for the process.

Target enrichment from a biological matrix was investigated for use with the left-handed PNA (two step) system. 10% (v/v) lithium-heparin collected whole blood and 10% saliva (final concentration) were tested with the assay. These biological samples were treated for RNase inhibition at a 50% (v/v) solution in PBS containing 20 mM ribonucleoside vanadyl complex (RVC). The samples were heated at 37° C. for 30 mins prior to dilution to 10% (v/v), in PBS containing 0.05% Tween 20 and the addition of either 1 μg of total human RNA (in blood samples) or 2 picomoles of Cy5 labelled synthetic 28base 18s rRNA (in saliva samples) and PNA probe. The PNA probe 'LH PNA-RH 458R' was hybridized to the RNA by heating at 37° C. for 10 mins. Following this 30 μg of LHc functionalized Dynabeads were added to the solution containing the hybridized RNA PNA and a further incubation step of 10 mins at 37° C. was performed to hybridize the LH PNA complement on the beads to the LH PNA on the probe. In the case of the blood sample, the captured 18s rRNA from total human RNA, on Dynabeads, was washed in PBST before the beads were placed in a PBST solution containing an Atto488 labelled achiral PNA. This fluorescent achiral PNA was available to bind to a site on the 18s RNA close to the 458R location. The fluorescent PNA was hybridized at 37° C. for 10 mins to the 18s on the Dynabeads. The Dynabeads were then washed again and the RNA eluted into a solution containing 10 mM potassium hydroxide and heated to 95° C. for 2 mins. The solutions that were eluted from the beads were read on a spectrophotometric plate reader at the excitation and emission wavelengths corresponding to the Atto488 dye that had been brought through the assay into the elution plate via hybridization to the 18s rRNA.

Figure 13:
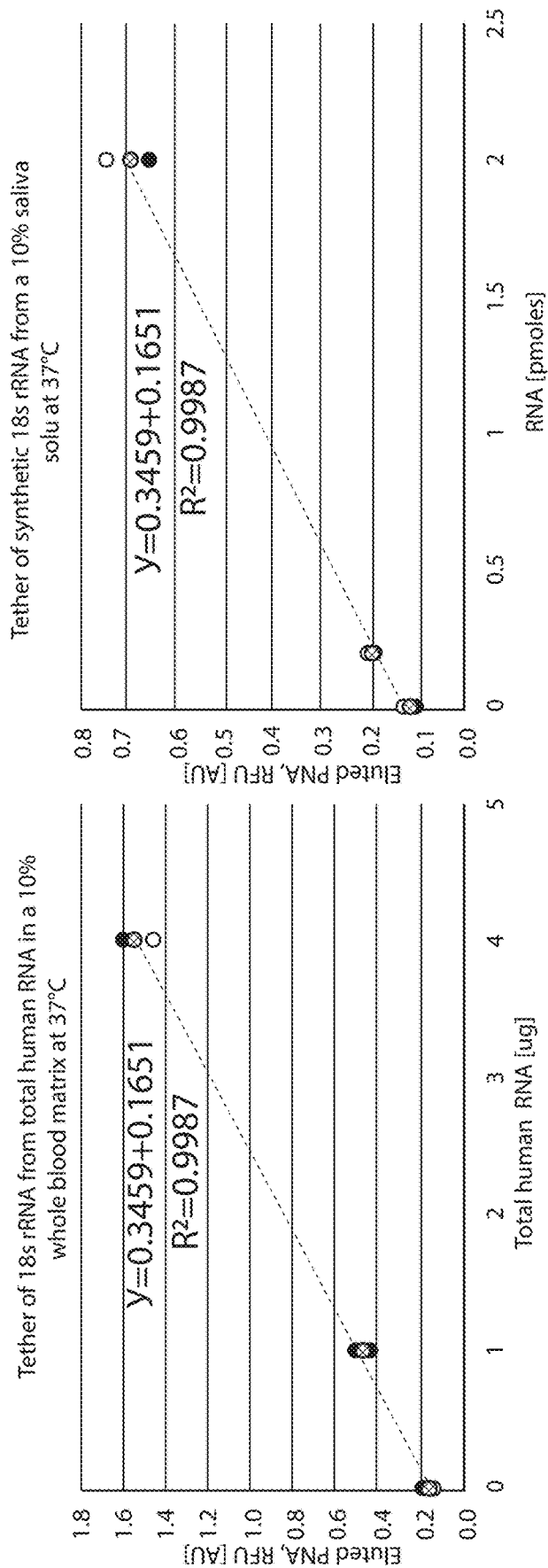
FIG. 13 shows data from detection of 18s RNA from a total human RNA.

FIG. 13 shows data from detection of 18s RNA from a total human RNA. In particular, FIG. 13 shows data from detection of 18s RNA from a total human RNA background and a 10% matrix of A) whole blood, and B) saliva, in which N=3 and the trend line is of the average values (dotted line) to illustrate use of left-handed PNA system. The left-handed PNA system provided for direct detection of 18s RNA and was observed from the samples. The data show detection of 18s rRNA from a total human RNA background and a 10% matrix of A) whole blood and B) detection of synthetic 18s RNA from a background of 10% saliva. N=3 the trend line is of the average values (dotted line).

Capture of 18s rRNA was obtainable from both biological solutions at 10% (v/v) using buffers of Phosphate Buffer Saline with 0.05% Tween 20 and using 8 mM of the RNase inhibitor RVC (final concentration). The linear trend of both graphs indicates that RNA capture is proportional to the PNA eluted in solution at the final step of the assay and that the assay can be applied to different sample types, depending on the application at hand. This shows that the two-step method is an advantageous alternative enrichment method to biotin-streptavidin.

Comparison to Biotin-Streptavidin

Figure 14:
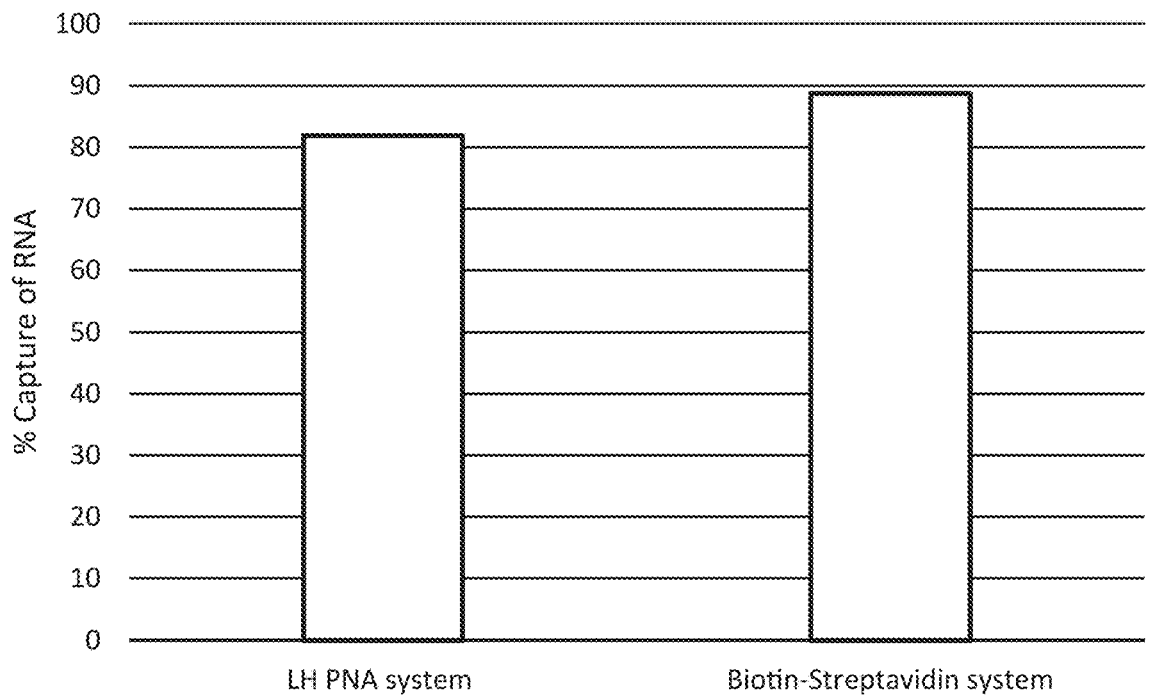
FIG. 14 are plots showing very similar performance of left-handed PNA capture of RNA compared to the prior biotin-streptavidin approach.

A capture assay was tested to directly measure the performance of a biotinylated PNA probe vs a left-handed PNA probe in the two-step method. For comparison the 'LH PNA-RH 458R' probe was compared with a biotinylated RH 458R probe which contained an identical right-handed PNA for the RNA target sequence. A Cy5 labelled 28 base synthetic 18s RNA was incubated with the biotinylated probe or the 'LH PNA-RH 458R' probe initially to hybridise for 10 mins at 37° C. before capture with 30 μg of streptavidin or complementary left-handed PNA functionalized 1 μm Dynabeads for a further 10 mins at room temperature. The capture assay was evaluated using fluorescence of the remaining RNA left in solution and measured on a plate reader. The results of the comparison assay are shown in FIG. 14, which shows a very similar performance of the left-handed PNA capture of RNA compared to the standard biotin-streptavidin approach. The results show a similar capture efficiency was achieved for both sets of RNA capture systems. This indicates that the two-step RNA capture method is comparable in target enrichment to the known biotin-streptavidin system.

Specificity of the Left-Handed PNA on Dynabeads with Nucleic Acids

Dynabeads functionalized with left-handed PNA were incubated with both a complementary Cy3 labelled synthetic RNA, and, a complementary FAM-labelled left-handed PNA. Due to the right-handed chirality of the RNA, only the left-handed PNA should bind to its complement, despite the RNA having the same sequence. The PNA and RNA were incubated together with the beads for 10 mins at 57° C. before removing and the fluorescence remaining in solution was measured for the efficiency of the capture. This experiment was repeated with the same complementary FAM-labelled PNA and a random, non-complementary Cy3 labelled RNA. Both sets of capture experiments were repeated with removal of the beads at room temperature. The results of the experiments are shown in FIG. 15, in which beads were removed from solution at room temperature, about 22° C., or at 57° C.

Figure 15:
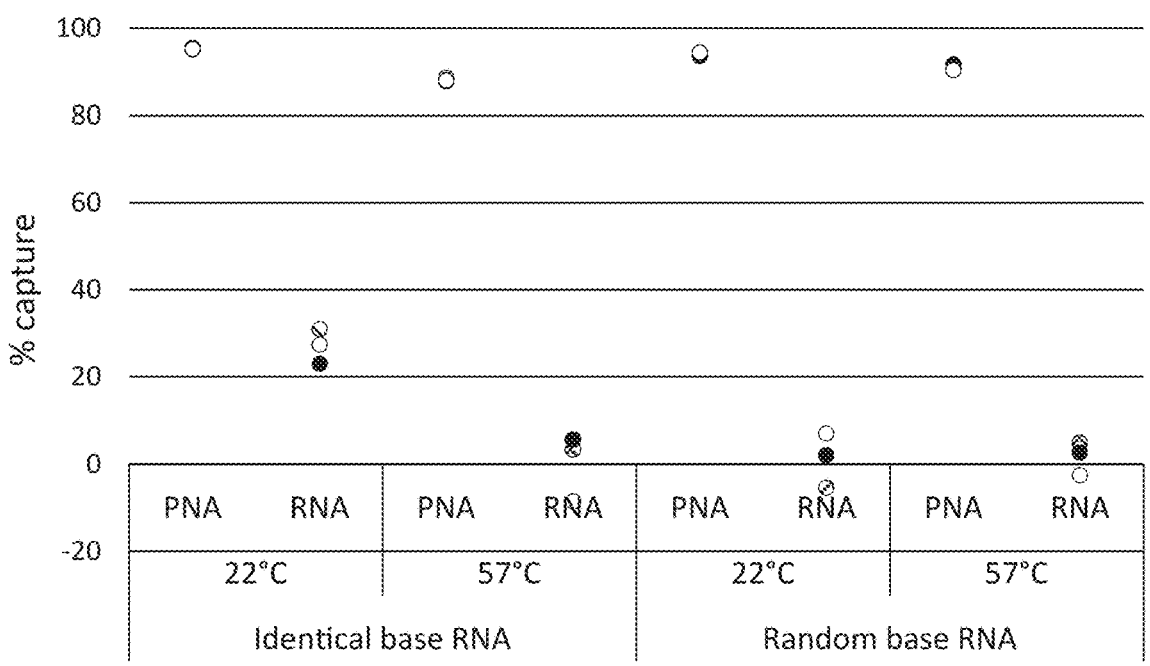
FIG. 15 shows capture data of left-handed and right-handed PNAs.

FIG. 15 shows capture data of left-handed and right-handed PNAs. In particular, FIG. 15 shows specific capture of left-handed PNA with complementary left-handed PNA on beads and little capture of the complementary RNA, due to the natural right-handed chirality of RNA. Less non-specific RNA capture is observed when the RNA sequence is a random sequence compared to the PNA sequence. Removing beads at 57° C. prevents identical base RNA binding to the beads.

From the experiment it can be observed that the left-handed PNA Dynabeads only specifically capture the PNA in solution and almost none of the right-handed RNA. This shows the abiotic nature of the left-handed PNA system. There is a small amount of capture when the beads are removed at room temperature and, in the worst-case scenario, where an RNA has the exact match of the left-handed PNA sequence. With the use of heat, as shown in FIG. 15, non-specific binding is eliminated and the left-handed PNA can capture its target sequence with only a slight reduction in capture. In the case where the RNA is not an exact match, it will not be captured by the left-handed PNA, even at room temperature, which shows the abiotic nature of the system.

Further Example

Figure 16:
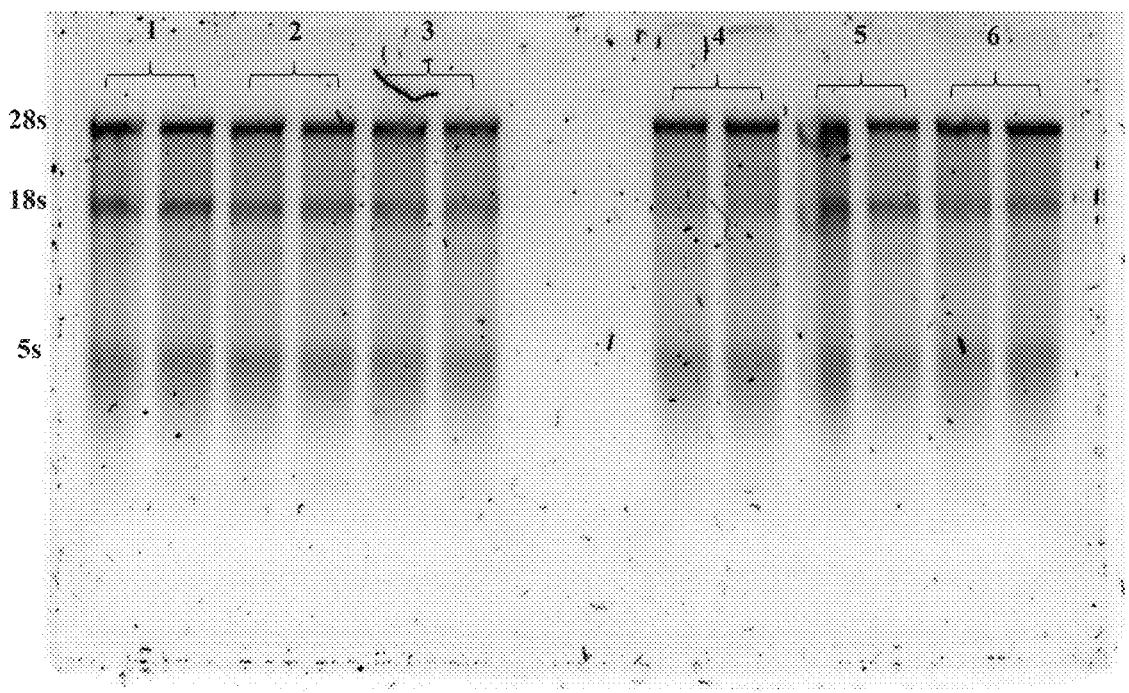
FIG. 16 shows an agarose gel of 18s ribosomal RNA depletion assay from a total human RNA sample.

Total human RNA samples were run out in duplicate on a 1% agarose gel via electrophoresis where the 18s ribosomal RNA was depleted with differently functionalized Dynabeads, as shown in FIG. 16. Sample 1 was a total human RNA standard in PBST. 2 was RNA incubated with 150 μg 458R RH beads. 3 was RNA incubated with 210 μg 458R RH beads. 4 was RNA incubated with 'LH PNA-458R RH' probe first, followed by 150 μg of LH PNA complement beads. 5 was a control with RNA incubated with 150 μg of streptavidin beads. 6 was RNA incubated with 20 'biotinylated 458R RH' probe first, followed by 150 μg of streptavidin beads.

All samples were incubated with 0.75 µg of total human RNA for 10 mins at 68° C. either with beads (lanes 2 and 3) or PNA probe (lanes 4 and 6) in PBST and cooled to 37° C. This was followed by 10 mins at 47° C. for 10 mins, with beads (lanes 4, 5 and 6).

Using Image J to analyze the gel, a grey value line profile was obtained for each lane of the gel in the vertical direction. First each lane was normalized to the concentration of RNA in the lane by using the area under the curve of the 28s rRNA bands. Then the area under the curve of the 18s rRNA bands was measured and compared to the RNA standard in lanes 1.

Lane 2 had a reduction in the 18s band of approx. 25% and an even greater reduction was observed in lanes 3 with 35%. The most contrasting difference was observed in lanes 4 with the LH PNA system where there was 70% removed from solution. Lanes 5 were used as a control for the streptavidin beads to evaluate if they were non-specifically binding RNA, of which approximately 20% was and lanes 6 are used with the biotinylated 458R RH probe where 40% of RNA was removed from solution.

The data showed that the LH PNA two step system performed better than the biotin-streptavidin two step system for removing 18s rRNA from a total human RNA isolate. It also outperformed Dynabeads that were functionalized directly with 458R RH PNA, where it appears that the two step is necessary to bind to larger, more structural RNA targets and successfully move them out of solution. The gel also showed that the PNA probe on the beads were specific for their 18s target as the 28s rRNA band remained largely unchanged in all lanes and was not removed from solution simultaneously.

Advantages

As avidin is a biological protein and is naturally occurring in biological samples, this invention provides an abiotic alternative to avidin for use in enriching or depleting RNA targets. This alternative can be used to contribute to the reduction of false positive results that are obtained when using biotin-avidin testing systems caused by endogenous biotin or dietary biotin. Alternatives to biotin tags that are offered in DNA synthesis include digoxigenin (DIG), cholesterol and dinitrophenyl (DNP). These are antigen-antibody based detection alternatives. In other applications, protein based binding systems can be used such as the maltose tag with maltose binding protein system and the chitin tag with a chitin binding protein. In most alternatives there is a biological entity required in the labelling or detection process which would require correct storage in a fridge or freezer to ensure biological viability. This is not required with the left-handed PNA system as it has been shown that PNA can be stored at room temperature for years.

There are also a limited number of these type of antigen-antibody/protein systems available, particularly, commercially available. Three DNA synthesis companies offered three alternates to biotin, however, only DIG or cholesterol tag options were available from two companies for RNA oligo labelling. This limits the amount of multiplexing that can be achieved using such systems. Using the LH PNA system with, for example, a LH PNA containing 12 monomers would allow the user to design 16,777,216 different left-handed PNAs that could potentially be used for different targets of interest with corresponding complementary PNA on beads or surfaces. These beads could be of different physical properties in terms of composition material and/or functionalization, as appropriate to the multiplexing application. As DNA and RNA do not bind to these LH PNAs because of chirality, the sequence used with the LH PNA system will not interfere even if the target nucleic acids are the same sequence as the LH PNAS, as long as the beads are removed at temperature in the assay for stringency (see FIG. 15).

One other advantage of using the LH PNA probe system is the LH PNA and complement can be designed to have a melt temperature at a particular temperature range. Target release through a programmable melt temperature allows the user to collect their target off the beads or surface without potentially damaging their target of interest. This removes the need for very harsh conditions to disassociate the target from the beads, unlike with biotin-streptavidin capture systems, which require a boiling step in 95% formamide at 65° C. for 5 mins or 2 mins at 90° C. to remove biotinylated nucleic acids. This step denatures the streptavidin conjugated to the magnetic beads to release the biotin molecule and the denaturation of streptavidin means that the beads cannot be reused. Magnetic beads coated with left-handed PNAs could be reused for other applications, if the probes used in both applications had the same left-handed PNA sequence and the previous probe was sufficiently heat melted off the beads prior to use with the new application.

It is also envisaged, in some examples, where one of the PNA pair is a left-handed PNA and one is a non-chiral PNA. The system could still be viable in such a scenario, however, smart design of the achiral PNA would have to be considered in order to avoid interaction with naturally occurring right-handed oligonucleotides, which achiral PNA can hybridize to, and could interfere with the complementary pair of PNAs.

It will be appreciated that capture of 18s RNA is more efficient when using the left-handed PNA capture system compared with achiral or right-handed PNA functionalized directly on beads. Direct detection of 18s RNA is feasible isothermally at 37° C. from biological samples, such as blood and saliva. The left-handed PNA enrichment system is an abiotic alternative to biotin-streptavidin based extraction systems and shows great potential for use in RNA and DNA applications in the future. Furthermore, as the sequence of the left-handed PNA can be readily changed the system is "programmable" with each new nucleic acid target being captured by a paired bead, which could potentially have different physical properties. This implies that these beads could be used as a versatile tool in many applications such as selection, depletion of a target, detection or multiplexing of analytes, antigens, nucleic acids or antibodies in methods that are well established like capture arrays, magneto-separation or even flow cytometry. This makes the left-handed PNA system a very multipurpose, adaptable and attractive system.

RNA targeting and amplification is traditionally done via enzymatic amplification methods such as Polymerase Chain Reaction (PCR). Correct storage and handling of reagents, such as enzymes, needed for such amplification is of great importance to ensure the biological integrity and, therefore, the success of the amplification process. Replacing these temperature sensitive and limited shelf life enzymes with abiotic alternatives for RNA enrichment is shown. Direct comparison showed that the left-handed PNA two-step method captured almost 4 times more 18s RNA from a total human RNA isolate than achiral or right-handed PNA functionalized directly on bead. The method has been shown to work isothermally at 37° C. and can be used in 10% biological matrices of whole blood or saliva without hindering capture of the 18s RNA. The LH system was also able to remove 18s rRNA from a total human RNA sample more successfully than the RH 458R functionalized beads or the biotin-streptavidin two step system, as visualized, on the agarose gel. This method poses a promising abiotic alternative to biotin-streptavidin based target enrichment.

The methods described herein circumvent some or all of the disadvantages with prior approaches, providing stable, strong but reversible affinity, programmability to bind multiple targets, or to a specific bead or part of a substrate, and which is stable in a range of temperature conditions and has little to no crosstalk with endogenous nucleic acids. We therefore believe that 20 the methods described herein have the potential to be transformative in this field.

Alternative Examples

The invention is not limited to the embodiments described but may be varied in construction and detail.

The targeting moiety on the first or second probe containing left-handed PNA and linker can be any one or more of the following, for example: a Peptide nucleic acid (achiral or chiral PNA); a deoxyribonucleic acid; a ribonucleic acid; a glycol nucleic acid; a threose nucleic acid; a locked nucleic acid; a phosphorothioate oligonucleotide; or a phosphorodiamidate Morpholino oligomer; a protein; a peptide; a peptide or protein with unnatural amino acids; an enzyme; an antibody; a single domain antibody (nanobody); an aptamer; a drug molecule; a small molecule; a chemical compound; a cell, or a combination of one or more of the above.

The detection moiety may be one or more of the following for example: a fluorescent label; a luminescent label; a chromophore label; a chemiluminescent label; a radioactive label, an enzyme label; or a visual label (e.g. a metallic label such as gold) a microsphere (magnetic, fluorescent, silica etc.); a nanoparticle (Carbon nanotube, Quantum Dot etc.); a biotin label; an avidin label; a digoxigenin, cholesterol, or dinitrophenyl label; a Horseradish peroxidase label; or a combination of one or more of the above.

In various examples the linker may: be of length 1-120 atoms; contain one or some of the elements: C, N, O, S, P, and Si; be in a chain that contains only one or a combination of the following bonds: a single bond/double bond/triple bond, an amide bond, an ester bond, a disulfide bond, an imino group, an ether bond, a thioether bond, and a thioester bond.

The left-handed PNA sequences are programmable to allow multiplexing, in that the sequences can be altered by length and/or monomer sequence to ensure they only interact with a sequence-specific complementary PNA on the surface and do not interact with each other or other nucleic acid sequences.

What is claimed is:

1. A method of target enrichment in a sample, the method comprising the steps of:
    introducing a probe comprising a left-handed PNA molecule linked to a capture moiety into a sample comprising target analyte;
    capturing, with the capture moiety, the target analyte; and
    binding the left-handed PNA molecule with a complementary PNA molecule comprising a left-handed chiral structure, the complementary PNA molecule being attached to a surface to thereby enrich for target analyte.

2. The method of claim 1, wherein the surface comprises a bead.

3. The method of claim 2, wherein the bead is a magnetic bead.

4. The method of claim 1, wherein the surface comprises a fixed substrate.

5. The method of claim 1, wherein the left-handed PNA molecule comprises a linker linking the left-handed PNA molecule to a targeting moiety.

6. The method of claim 1, wherein the method further includes introducing a second probe into the sample, said second probe comprising a left-handed PNA, a targeting moiety, and a detection moiety.

7. The method of claim 6, wherein the targeting moiety is a right-handed targeting PNA.

8. A method of claim 1, wherein the capture moiety comprises an antibody or an antibody fragment.

9. The method of claim 1, wherein the method is carried out at a temperature in the range of 18° C. to 80° C.

10. The method of claim 9, wherein the method is carried out at a temperature of about 37° C.

11. The method of claim 1, wherein the target analyte comprises RNA.

12. The method of claim 11, wherein the RNA comprises 18s ribosomal RNA.

13. The method of claim 1, wherein the surface comprises a surface of a bead, and said method further comprises after the binding step, heat the bead to provide a clean capture surface for re-use in a further assay.

14. The method of claim 1, wherein the capture moiety comprises any one or more of an achiral or chiral PNA, a deoxyribonucleic acid, a ribonucleic acid, a glycol nucleic acid, a threose nucleic acid, a locked nucleic acid, a phosphorothioate oligonucleotide, a phosphorodiamidate morpholino oligomer, a protein, a peptide, a peptide or protein with unnatural amino acids, an enzyme, an antibody, a single domain antibody, an aptamer, a drug molecule, a small molecule, a chemical compound, a cell, or a combination of one or more of the above.

15. The method of claim 1, wherein a detection moiety is linked with the left-handed PNA molecule, and the detection moiety includes one or more of the following: a fluorescent label, a luminescent label, a chromophore label, a chemiluminescent label, a radioactive label, an enzyme label, a visual label, a metallic label, a microsphere, a nanoparticle, a biotin label, an avidin label, a digoxigenin label, a cholesterol label, a dinitrophenyl label, a Horseradish peroxidase label, or a combination of one or more of the above.

16. The method of claim 1, wherein the a left-handed PNA molecule comprises a linker, and the linker comprises a length of 1 to 120 atoms, and/or has one or some of the elements: C, N, O, S, P, and Si, and/or is in a chain that contains only one or a combination of the following bonds: a single bond, a double bond, a triple bond, an amide bond, an ester bond, a disulfide bond, an imino group, an ether bond, a thioether bond, and a thioester bond.

* * * * *